United States Patent [19]
Komatsu et al.

[11] Patent Number: 5,490,194
[45] Date of Patent: Feb. 6, 1996

[54] METHOD AND APPARATUS FOR ANALYZING CONTAMINATIVE ELEMENT CONCENTRATIONS

[75] Inventors: Fumio Komatsu, Fuchu; Kunihiro Miyazaki, Tokyo; Ayako Shimazaki, Yokohama, all of Japan

[73] Assignee: Kabushiki Kaisha Toshiba, Kawasaki, Japan

[21] Appl. No.: 348,928

[22] Filed: Nov. 25, 1994

[30] Foreign Application Priority Data

Nov. 25, 1993 [JP] Japan .................... 5-295405

[51] Int. Cl.$^6$ .................................................. G01N 23/223
[52] U.S. Cl. ........................ 378/45; 378/44; 378/207
[58] Field of Search .................... 378/44, 45, 49, 378/50, 207, 57, 58

[56] References Cited

U.S. PATENT DOCUMENTS

| | | | |
|---|---|---|---|
| 5,249,216 | 9/1993 | Ohsugi et al. | 378/44 |
| 5,422,925 | 6/1995 | Komatsu et al. | 375/45 |

OTHER PUBLICATIONS

Patent Abstracts of Japan, vol. 17, No. 461 (P–1598), Aug. 23, 1993, JP–5–107363, Apr. 27, 1993.
Patent Abstracts of Japan, vol. 17, No. 122 (P–1501), Mar. 15, 1993, JP–4–305149, Oct. 28, 1992.
Patent Abstracts of Japan, vol. 18, No. 420 (P–1782), Aug. 5, 1994, JP–6–13004, May 13, 1994.
Patent Abstracts of Japan, vol. 18, No. 349 (P–1763), Jun. 30, 1994, JP–6–088792, Mar. 29, 1994.
Nuclear Instruments and Methods, vol. 128, No. 2, Oct. 1975, pp. 359–362, Joachim Knoth, et al., "A Simple Method for Peak Area Determination of Doublets".
International Journal of Applied Radiation and Isotopes, vol. 26, No. 10, Oct. 1975, pp. 626–629, F. Steger, et al., "Two–Area–Method For Evaluating Scintillation Gamma Spectra By Calibrated Peak Fractions".
Nuclear Instruments & Methods in Physics Research, vol. 199, No. 3, Aug. 1982, pp. 509–519, V. B. Zlokazov, "Method For An Automatic Peak Search In Gamma–Ray Spectra".

*Primary Examiner*—David P. Porta
*Assistant Examiner*—Don Wong
*Attorney, Agent, or Firm*—Oblon, Spivak, McClelland, Maier & Neustadt

[57] ABSTRACT

In the method and apparatus for analyzing contaminative element concentrations, a fluorescent X-ray generated by elements when an X-ray is total reflected from the surface of a substrate is detected by a fluorescent X-ray detector; a peak of the fluorescent X-ray generated by a substrate element and peaks of the fluorescent X-ray generated by other contaminative elements are separated from the detected fluorescent X-ray waveform by a peak separating circuit; and the concentrations of the detected contaminative elements are calculated on the basis of the separated peaks by a calculating circuit. In the peak detection, in particular, the peaks of the contaminative elements to be analyzed are detected from the waveform. When other peaks are present within a predetermed number of channels (energy eV) before and after each detected peak, the channel numbers and the signal intensities between the respective peaks are extracted. Further, the a true peak is determined after obtaining the evaluation values of the respective peaks, so that it is possible to separate peaks from the fluorescent X-ray waveform accurately, even if each peak is split in the observed waveform.

4 Claims, 6 Drawing Sheets

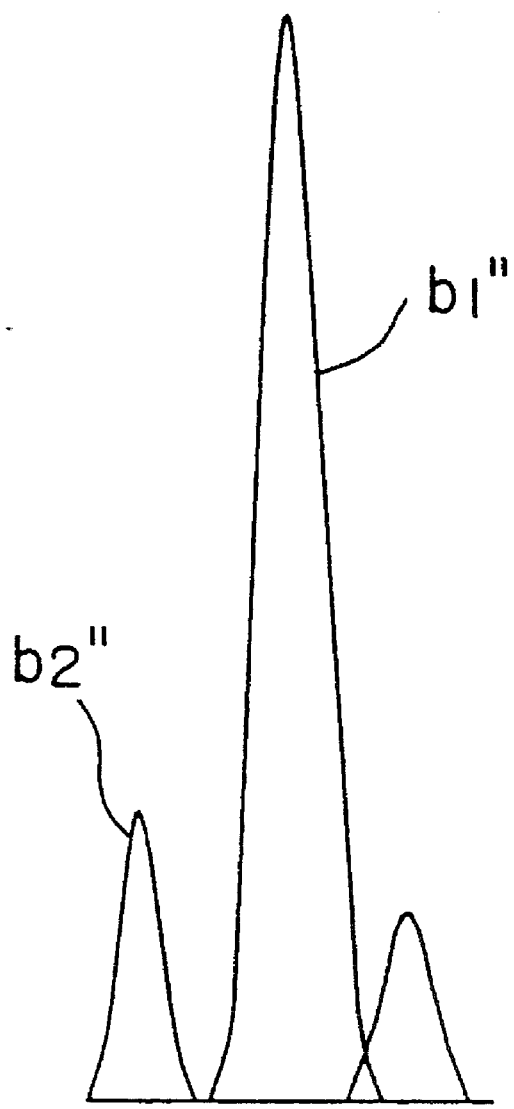
F I G. 3

METHOD AND APPARATUS FOR ANALYZING CONTAMINATIVE ELEMENT CONCENTRATIONS

BACKGROUND OF THE INVENTION

1. Field of the Invention

The present invention relates to a method and an apparatus for analyzing contaminative element concentrations, and more specifically to a method and an apparatus for measuring contaminative element concentrations on a semiconductor substrate, for instance with the use of an energy dispersive type total refection X-ray fluorescence analysis.

2. Description of the Background Art

Conventionally, as a non-destructive contaminative element concentration analyzing apparatus, there is so far known a total reflection X-ray fluorescence analysis (See "Inspection, Analysis and Measurement Technology Required 16M/64M Integration or After", by Ayako SIMAZAKI, Kunihiro MIYAZAKI; NIKKEI MICRODEVICE, No. 86, pages 148, 154, 156 and 158, August, 1992). Furthermore, as a contaminative element concentration analyzing apparatus based upon total reflection X-ray fluorescence analysis, an energy or wavelength dispersive type apparatus is known. Since the contaminative element concentrations can be analyzed nondestructively with the use of the contaminative element concentration analyzer based upon the total reflection X-ray fluorescence analysis, it has become possible to manage the contamination of silicon wafer during the semiconductor manufacturing process, and thereby the contamination of wafer can be reduced effectively.

FIG. 4 is a conceptual block diagram showing an example of the contaminative element concentration analyzer using the energy dispersive type total reflection X-ray fluorescence analysis.

In FIG. 4, a sample base 4 is mounted within a vacuum chamber 41, and a sample (e.g., silicon wafer) 43 is mounted on this sample base 2. an X-ray generated by a rotating pair-cathode type X-ray source 4 is converted to a monochromatic ray through a monochrometer 45, being passed through a slit 49, and then allowed to be incident upon the sample 43 at a small total-reflection angle. On the basis of this incident X-ray, a fluorescent X-ray can be generated from the surface of the sample 43. The generated fluorescent X-ray is detected by a detector (e.g., semiconductor detector), and converted into electric signals corresponding thereto. The fluorescent X-ray signals detected as described above are processed by a pulse processor 47 to obtain an observed waveform as shown in FIG. 5. In FIG. 5, the abscissa designates the energy of the detected fluorescent X-ray and the ordinate designates the signal intensity (relative intensity according to the number of photons incident upon the detector 46) of the detected fluorescent X-ray. FIG. 5 indicates that the observed waveform (graph) has a peak value for each element (silicon and other contaminative elements) contained in the silicon wafer 43. In addition, the integral intensity (which corresponds to an area of a peak waveform) of each peak is proportional to the concentration of the element.

On the other hand, an arithmetic processing circuit 48 stores information indicative of the relationship between the integral intensity of the fluorescent X-ray and the concentration for each contaminative element, which is referred to as "analytical curve". Therefore, the arithmetic processing circuit 48 first separates the peaks of the contaminative elements from the observed waveform (See FIG. 5) inputted by the pulse processor 47 for concentration detection, and then calculates the respective integral intensities of the separated peaks, and obtains the contaminative element concentrations on the basis of the integral intensities and the analytical curves.

A co-pending U.S. Patent Application Ser. No. 08/116,750 now U.S. Pat. No. 5,422,925 which is incorporated herein discloses a method of peak separation.

Here conventionally, the peaks of the contaminative elements have been separated as follows:

(1) First, the respective peaks are detected on the basis of the observed waveform (See FIG. 5). In this peak detection, the observed waveform is first processed for smoothing differentiation to obtain third-order differentiated waveform. After that, zero points are detected from the obtained three-degree differentiated waveform, and further the peaks are detected from these detected zero points under the conditions that the quadratic differential value is minimized and further the fluorescent X-ray intensity of the observed waveform exceeds a predetermined value.

(2) Furthermore, for each of the respective detected peaks, a tentative value such as a peak position, a peak height, a half width of half maximum (a deviation of a point on the distribution curve at a half value of the peak height from the average value), etc. are set.

(3) The respective peaks are processed for nonlinear optimization in accordance with a model function having the peak position, the peak height, and the half width of half maximum as parameters (by using the above-mentioned tentative values as initial values), and further such a peak position, a peak height and a half width of half maximum that a differential square sum between the model function and the observed waveform can be minimized are obtained, respectively. In accordance with the method as described above, it is possible to separate the respective required peaks of the contaminative elements from the observed waveform.

In the above-mentioned peak separating method of the conventional contaminative element concentration analyzing apparatus, however, there the observed waveform is distorted; that is, the waveform peak is split, there exists such drawbacks that a plurality of peaks are superposed upon each other. For instance, FIG. 6A shows an observed waveform of Fe and Ni (which corresponds to the energy range between 6.89 and 8.01 eV in FIG. 5)), and a1 denotes the peak waveform of Kα of Ni and a2 denotes the peak waveform of Kβ ray of Fe, respectively. In the case where there exist such peak splits, the peak a1 shown in FIG. 6A is discriminated as two peaks b1 and b1' superposed upon each other, and the peak a2 shown in FIG. 6A is discriminated as two peaks b2 and b2' superposed upon each other, as shown in FIG. 6B.

In the case of the conventional method, the fact that the waveform having peak splits is discriminated as two peak superposition is a normal discrimination result. However, in practice, since there exists no such peak superposition, this implies that the number of peaks is detected erroneously.

Further, where the waveform having peak splits is discriminated as a plurality of peaks superposed upon each other, since the respective peak heights or the respective half widths of half maximum of the detected peaks are inevitably produced erroneously, when the integral intensities of the peaks are calculated at the succeeding stage, an error occurs, so that the analysis results of the concentrations are not accurate.

SUMMARY OF THE INVENTION

Accordingly, the object of the present invention is to provide a method and an apparatus for analyzing the contaminative element concentrations, which can separate the peaks of the observed waveform accurately even if the peak is split.

According to one aspect of the present invention, there is provided a method of analyzing contaminative element concentrations, comprising the steps of:

irradiating an X-ray upon a substrate to be analyzed at a predetermined incident angle;

detecting an observed waveform of fluorescent X-ray generated by elements when the irradiated X-ray is total reflected from the substrate surface to be analyzed;

detecting a peak of a contaminative element to be analyzed from the obtained observed waveform;

detecting presence or absence of other peaks within a predetermined number of channels before and after the detected peak;

when the other peaks are detected, extracting channel numbers and signal intensities between the respective detected peak positions;

calculating evaluation values Yi on assumption that the respective detected peaks are true peaks in accordance with $$Yi = \Sigma i |P - Pi|x\, Ci$$

where

P: channel number of the tentative peak

Pi: channel number between peaks

Ci: signal intensity at channel number Pi comparing the calculated evaluation values Yi with each other to discriminate the true peak having the minimum evaluation value Yi as a true peak;

separating the peak of contaminative element to be analyzed from the observed waveform on the basis of the discriminated peak; and calculating a concentration of the contaminative element to be analyzed on the basis of the separated peak.

According to another aspect of the invention, there is also provided a contaminative element concentration analyzing apparatus, comprising:

X-ray irradiating means for irradiating an X-ray upon a substrate to be analyzed at a predetermined incident angle;

X-ray detecting means for detecting fluorescent X-ray generated by elements when the irradiated X-ray is total reflected from a surface of the substrate, to obtain an observed waveform;

peak separating means for separating peaks of the fluorescent X-ray generated by contaminative elements to be analyzed from the fluorescent X-ray waveform detected by said X-ray detecting means; and concentration detecting means for detecting concentration of the contaminative elements to be analyzed on the basis of the peaks separated by said separating means, wherein said separating means comprises:

first detecting means for detecting a peak of the detected contaminative element from the waveform detected by said X-ray detecting means;

second detecting means for detecting presence or absence of other peaks within a predetermined number of channels before and after the peak detected by said first detecting means;

extracting means, when said second peak detecting means detects other peaks, for extracting the numbers of channels and signal intensities between the respective peaks;

evaluation value calculating means for calculating evaluation values Yi on assumption that the respective detected peaks are true peaks in accordance with $$Yi = \Sigma i |P - Pi|x\, Ci$$

peak discriminating means for comparing the evaluation values Yi calculated by said evaluation calculating means with each other to discriminate the peak having the minimum evaluation value Yi as a true peak.

In the present invention, first peak detecting means and second peak detecting means discriminate whether there exist a plurality of peaks in close vicinity. In the case where there exist a plurality of peaks in close vicinity, the respective evaluation values Yi are calculated by evaluation value calculating means. Furhter, the calculated evaluation values Yi are compared with each other by peak discriminating means, and only when the evaluated value Yi is the minimum, the peak is discriminated as a true peak. Therefore, even if there exists a peak split or peak splits in the observed waveform, it is possible to separate peaks accurately.

BRIEF DESCRIPTION OF THE DRAWINGS

In the attached drawings:

FIG. 3 is a graphical representation for assistance in explaining the precessed results of the peak separating circuit shown in FIG. 1;

DETAILED DESCRIPTION OF THE PREFERRED EMBODIMENTS

An embodiment of the present invention will be described hereinbelow by taking the case where contaminative elements on the surface of a silicon wafer (as the substrate to be measured) are analyzed.

Figure 1:
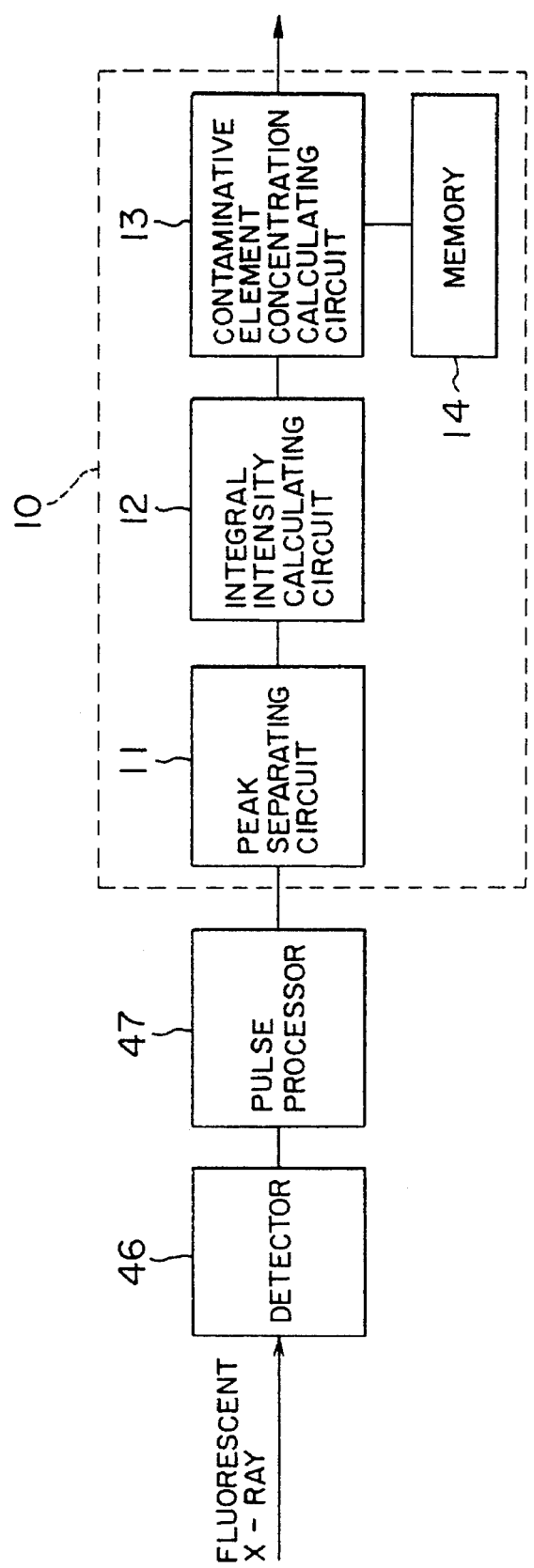
FIG. 1 is a block diagram showing a detector and an arithmetic processing circuit of an embodiment of the contaminative element concentration analyzing apparatus according to the present invention.
Figure 2:
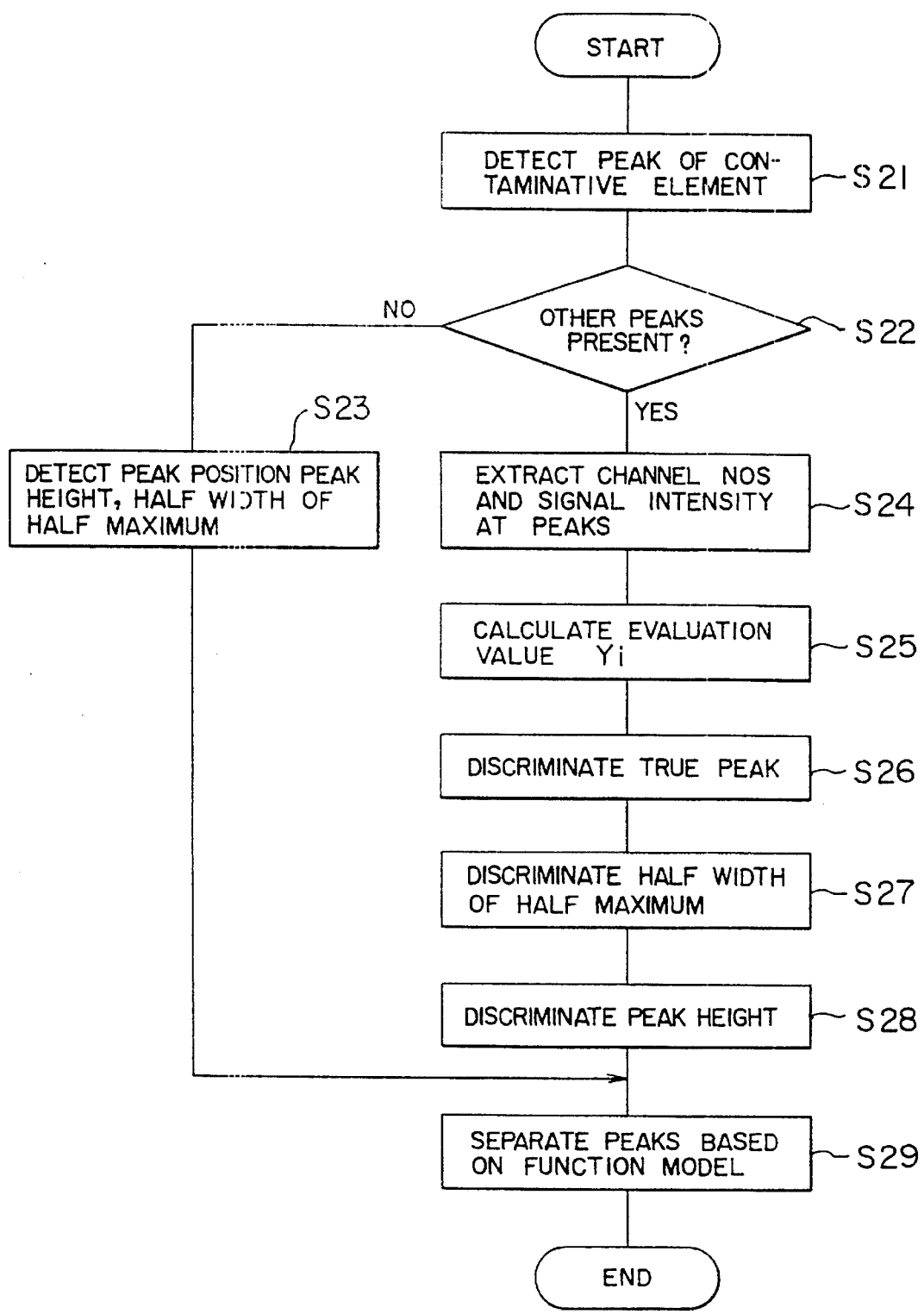
FIG. 2 is a flowchart for assistance in explaining the processing procedure of a peak separating circuit shown in FIG. 1.
Figure 4:
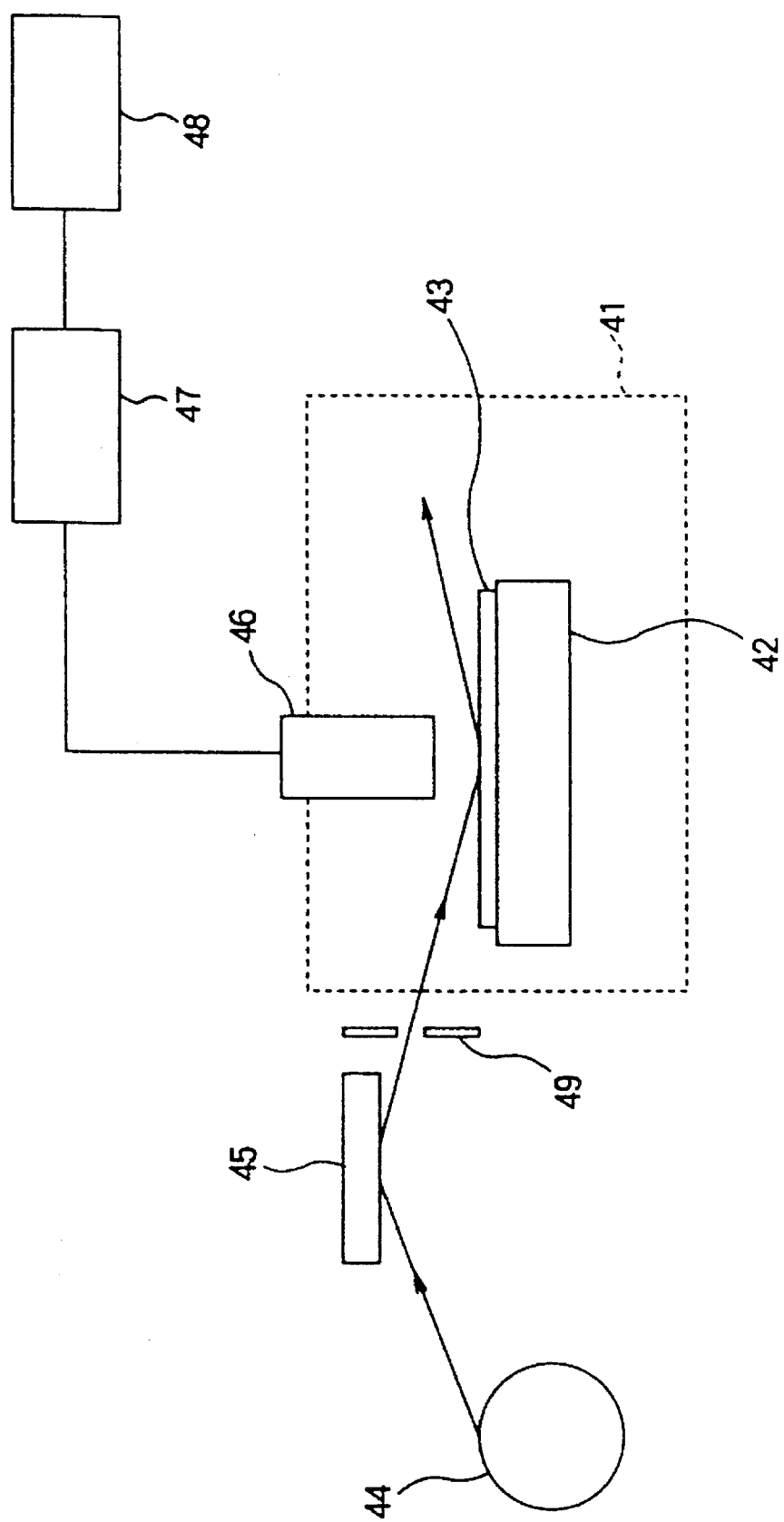
FIG. 4 is a conceptual block diagram showing an example of the conventional contaminative element concentration analyzing apparatus.
Figure 5:
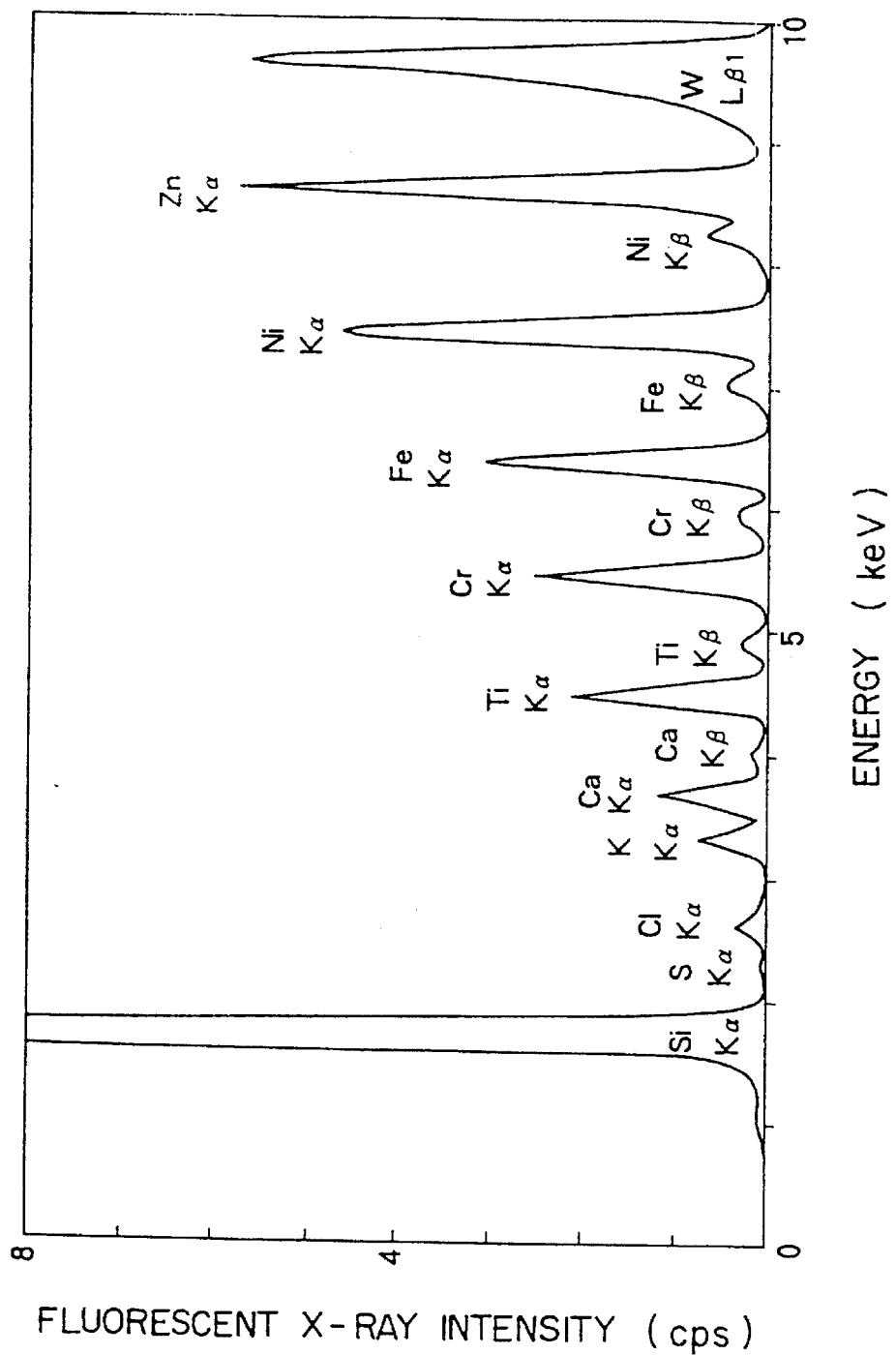
FIG. 5 is a graphical representation showing the output waveform of the pulse processor shown in FIG. 4.

FIG. 1 is a block diagram showing a detector and an arithmetic processing circuit of the contaminative element concentration analyzing apparatus according to the present invention, which corresponds to the processing section after the detector in FIG. 4. FIG. 2 is a flowchart for assistance in explaining the operation of the peak separating circuit shown in FIG. 1.

In the present invention, only the arithmetic procedure of the peak separation processing executed by the arithmetic processing circuit 10 is different from that of the conventional apparatus shown in FIG. 4, and the construction and operation other than the above are the same as with the case of the conventional apparatus shown in FIG. 4.

The fluorescent X-ray generated from the surface of the silicon wafer 43 is allowed to be incident upon a detector (which corresponds to fluorescent X-ray detecting means of the present invention) 46 for instance such as a semiconductor detector. The detector 46 converts the intensity of the incident fluorescent X-ray into electric signal levels, and outputs the converted signal levels. The signal levels are inputted to a pulse processor 47 to obtain the observed waveform in the same way as with the case of the conventional case (See FIG. 4).

The obtained observed waveform is supplied to a peak separating circuit 11 of an arithmetic processing circuit 10. This peak separating circuit 11 separates peaks to be detected for concentration analysis from the supplied observed waveform, as described later in further detail.

The respective peak information separated as described above is inputted to an integral intensity calculating circuit 12. This integral intensity calculating circuit 12 calculates the integral intensities of the peaks of the respective contaminative elements. The calculated integral intensities are transmitted to the contaminative element concentration calculating circuit 13.

The contaminative element concentration calculating circuit 13 determines each contaminative element concentration corresponding to each inputted integral intensity on the basis of each analytical curve stored in a memory 14, and outputs the determined concentrations, respectively.

The peak separating circuit 11 shown in FIG. 1 will be described in detail hereinbelow.

FIG. 2 is a flowchart showing the processing procedure of the peak separating circuit 11.

First, when the observed waveform is inputted from the pulse processor 47 to the peak separating circuit 11, the peak separating circuit 11 detects the peaks of contaminative elements to be analyzed from the inputted observed waveform (in step S21). In this peak detection, the observed waveform is first processed for smoothing differentiation to obtain the three-degree differentiated waveform. After that, zero points are detected from the three-degree differentiated waveform. Further, points of the detected zero points are selected under the conditions that the quadratic differential value becomes minimum and in addition the fluorescent X-ray intensity of the observed waveform exceeds a predetermined value (10% of the maximum value within the detection range in this embodiment).

Next, the peak separating circuit 11 detects whether there exist other peaks within 10 channels (e.g., one channel implies an energy range of 10 eV in this embodiment) before and after the peak now detected in step S21 (in step S22). When there exists no peak within the 10 channels before and after the detected peak, tentative values such as a peak value, a peak height, a half width of half maximum, etc. of the detected peak are detected (in step S23), and then executes the step S29 (described later).

On the other hand, in step S22, when there are other peaks within 10 channels, the channel numbers and the signal intensities between the respective peaks are extracted (in step S24). Further, the respective evaluation values $Y_i$ are calculated on the assumption that these respective peaks are true peaks as follows (in step S25):

$$Y_i = \Sigma_i |P - P_i| \times C_i$$

where

P: channel number of the tentative peak

Pi: channel number between peaks

Ci: signal intensity at channel number Pi

Further, the respective evaluation values $Y_i$ calculated as described above are compared with each other, and the peak having the minimum evaluation value $Y_i$ is discriminated as the true peak, and the peak position of the discriminated true peak is obtained (in step S26).

Further, the half width of half maximum of the peak thereof is discriminated (in step S27). In this embodiment, the maximum half width of half maximum in the peaks detected in steps S21 and S22 is determined as the true half width of half maximum.

After that, the peak height is discriminated (in step S28). In this embodiment, the peak height Px is calculated as follows:

$$Px = Pp \times (AO/Ag)$$

where

Pp: signal intensity at true peak decided in step S26;

AO: area at the peak in the waveform

Ag: area at the peak in the model waveform

Here, the model waveform can be constructed by using the Gaussian function.

Further, with the use of the model function having the peak position, peak height and half-value half-width as parameters, non-linear optimization processing (e.g., simplex method) is executed by setting the respective values obtained in steps S26 to S28 as the initial values. Further, such peak position, peak height and half width of half maximum that the differential square sum between model function and the observed waveform can be minimized, respectively are obtained (in step S29). As described above, it is possible to separate peaks of the contaminative elements required to be analyzed.

Figures 6A, 6B:
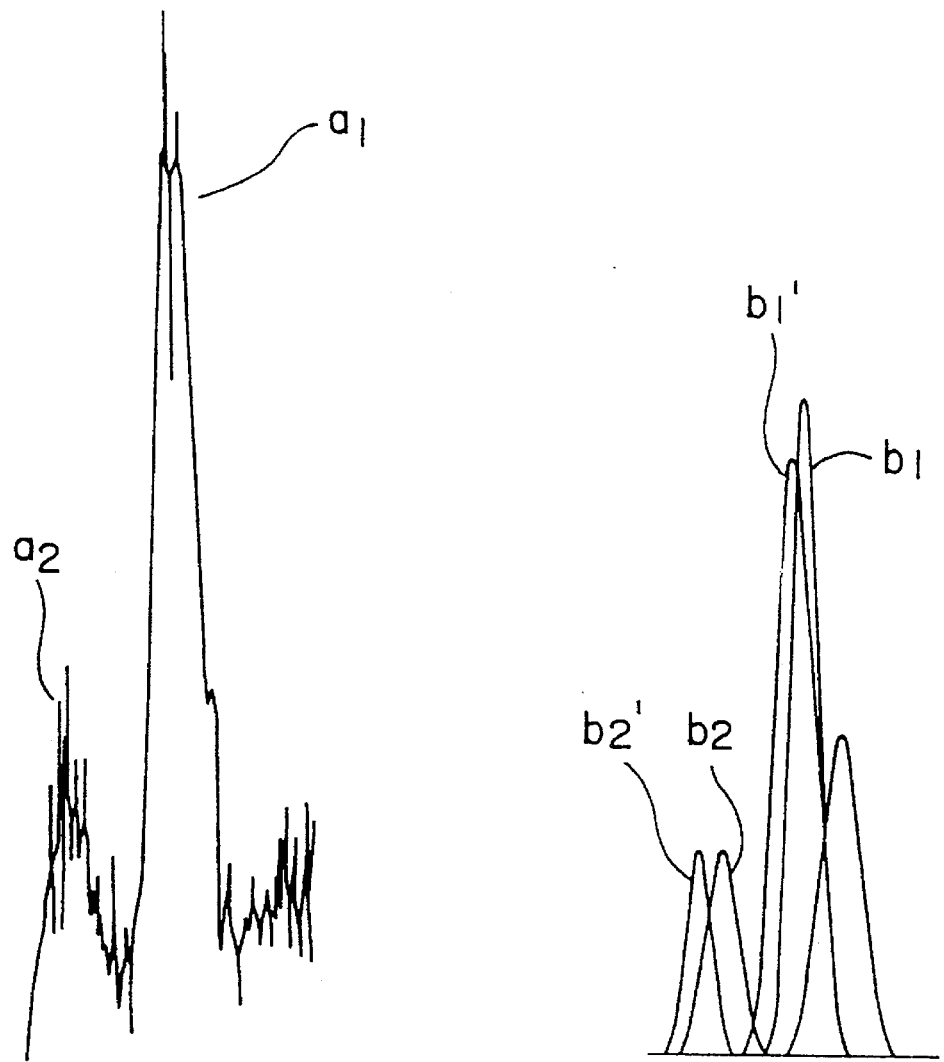
FIG. 6A is a graphical representation shownig a part of the output waveform of the pulse procesor shown in FIG. 4.
FIG. 6B is a graphical representation showing the results of peak separation of the output waveform shown in FIG. 6A.

FIG. 3 shows an example of the results obtained by separating the peaks of the observed waveform as shown in FIG. 6A by use of the peak separating circuit 11 of the present invention. In FIG. 3, b1" denotes the waveform obtained by the peak separation from the Kα ray a1 of Ni (shown in FIG. 6A), and b2" denotes the waveform obtained by the peak separation from the Kβ ray a2 of Fe (shown in FIG. 6A).

As a result of the peak separation of the observed waveform as shown in FIG. 6A with the use of the peak separating circuit 11 of the present invention, the half width half maximum of the Kβ ray of Fe is 170 eV, and the half width of half maximum of the Kα ray of Ni is 180 eV. These values are considered to be appropriate when taking into account the energy resolution of the fluorescent X-ray detecting means.

Further, where there exists a peak split, the peaks are offset from each other by several channels in the conventional apparatus. In the present invention, however, the peak position of the Kβ ray of Fe is 6.398 KeV and the peak position of the Kα ray of Ni is 7.470 KeV, without causing any the peak position offset.

As described above, in the present invention, even if the waveform is distorted; that is, the peak is split in the form of the waveform, since the peak is not discriminates as a plurality of peaks superposed upon each other, it is possible to prevent the peak separating circuit from detecting a plurality of peaks erroneously. Further, since the discrimination errors of the peak height and the half-value half-width caused by the erroneous discrimination as peak superposition can be prevented, it is possible to eliminate the error produced when peak integral intensity is calculated by the integral intensity calculating circuit 12 (See FIG. 1), thus improving the precision of analyzing the contaminative element concentration.

Further, in the present embodiment, although the simplex method has been adopted as the non-linear optimization method, it is possible to adopt anther method such as DFP.

Further, in the present embodiment, one channel is determined to be 10 eV, and the presence or absence of another peak is discriminated within 10 channels before and after the peak detected in step S21 (in step S22). However, the width of one channel and the width (the number of channels) for detecting the presence or absence of another peak are not limited only thereto. That is, it is possible to set one channel as 5 eV or to detect another peak existing within 20 or 100 channels before and after the detected peak. In other words, the above-mentioned width for detecting another peak can be determined freely according to the discrete width of the peaks of the respective contaminative elements, so that these widths are not limitative to the present invention.

As described above, in the contaminative element concentration analyzing apparatus according to the present invention, even if there exists a peak split in the observed waveform, it is possible to separate the peaks from the observed waveform accurately. Therefore, according to the present invention, it is possible to provide a contaminative element concentration analyzing apparatus of higher precision.

What is claimed is:

1. A method of analyzing contaminative element concentrations, comprising the steps of:

irradiating an X-ray upon a substrate to be analyzed at a predetermined incident angle;

detecting an observed waveform of fluorescent X-ray generated by elements when the irradiated X-ray is total reflected from the substrate surface to be analyzed;

detecting a peak of a contaminative element to be analyzed from the obtained observed waveform;

detecting presence or absence of other peaks within a predetermined number of channels before and after the detected peak;

when the other peaks are detected, extracting channel numbers and signal intensities between the respective detected peak positions;

calculating evaluation values Yi on assumption that the respective detected peaks are true peaks in accordance with $$Yi = \Sigma i |P - Pi| \times Ci$$

where

P: channel number of the tentative peak

Pi: channel number between peaks

Ci: signal intensity at channel number Pi comparing the calculated evaluation values Yi with each other to discriminate the true peak having the minimum evaluation value Yi as a true peak;

separating the peak of contaminative element to be analyzed from the observed waveform on the basis of the discriminated peak; and calculating a concentration of the contaminative element to be analyzed on the basis of the separated peak.

2. The method of analyzing contaminative element concentration of claim 1, which further comprises the steps of:

deciding a maximum deviation from its peak position within deviations at half values of respective detected peaks, as a true half width of half maximum; and calculating a peak height Px in accordance with $$Px = Pp \times (AO/Ag)$$

where

Pp: signal intensity at the true peak decided;

AO: peak area at the peak in waveform

Ag: peak area at the peak in model waveform

3. A contaminative element concentration analyzing apparatus, comprising:

X-ray irradiating means for irradiating an X-ray upon a substrate to be analyzed at a predetermined incident angle;

X-ray detecting means for detecting fluorescent X-ray generated by elements when the irradiated X-ray is total reflected from a surface of the substrate, to obtain an observed waveform;

peak separating means for separating peaks of the fluorescent X-ray generated by contaminative elements to be analyzed from the fluorescent X-ray waveform detected by said X-ray detecting means; and concentration detecting means for detecting concentrations of the contaminative elements to be analyzed on the basis of the peaks separated by said separating means, wherein said separating means comprises:

first detecting means for detecting a peak of the detected contaminative element from the waveform detected by said X-ray detecting means;

second detecting means for detecting presence or absence of other peaks within a predetermined number of channels before and after the peak detected by said first detecting means;

extracting means, when said second peak detecting means detects other peaks, for extracting the numbers of channels and signal intensities between the respective peaks;

evaluation value calculating means for calculating evaluation values Yi on assumption that the respective detected peaks are true peaks in accordance with $$Yi = \Sigma i |P - Pi| \times Ci$$

where

P: channel number of tentative peaks

Pi: channel number between the peaks

Ci: signal intensity at channel number Pi; and peak discriminating means for comparing the evaluation values Yi calculated by said evaluation calculating means with each other to discriminate the peak having the minimum evaluation value Yi as a true peak.

4. The contaminative element concentration analyzing apparatus of claim 3, which said peak separating means further comprises:

half width of half maximum discriminating means for discriminating the maximum deviation within deviations at half values of respective detected peaks, as a true half width of half maximum; and peak height calculating means for calculating a peak height Px in accordance with $$Px = Pp \times (AO/Ag)$$

where

Pp: signal intensity at the true peak decided by said peak discriminating means;

AO: area of the peak in waveform

Ag: area of the peak in model waveform.

* * * * *